United States Patent [19]

Hozumi

[11] 4,286,161
[45] Aug. 25, 1981

[54] FILM CASSETTE DRIVE MECHANISM IN DENTAL RADIOGRAPHIC APPARATUS FOR PHOTOGRAPHING ENTIRE JAWS

[75] Inventor: Kazuo Hozumi, Joyo, Japan

[73] Assignee: Kabushiki Kaisha Morita Seisakusho, Kyoto, Japan

[21] Appl. No.: 121,499

[22] Filed: Feb. 14, 1980

[30] Foreign Application Priority Data

Feb. 14, 1979 [JP] Japan .................. 54/18384[U]

[51] Int. Cl.³ .............................................. A61B 6/14
[52] U.S. Cl. .................................................. 250/439 P
[58] Field of Search ..................................... 250/439 P

[56] References Cited

U.S. PATENT DOCUMENTS 4,039,837  8/1977  Ohta et al. ................ 250/439 P
4,247,779  1/1981  Ciavattoni et al. ......... 250/439 P Primary Examiner—Alfred E. Smith
Assistant Examiner—T. N. Grigsby
Attorney, Agent, or Firm—Koda and Androlia

[57] ABSTRACT

The disclosure relates to a film cassette drive mechanism in a dental radiographic apparatus for photographing the entire jaws which apparatus is used in tomography. The drive mechanism is of such construction that a film cassette disposed at one end of a rotary arm of the apparatus in an opposed relation with respect to an X-ray source disposed at the other end thereof is moved to feed a film necessary for tomography by driving a variable speed motor inside the cassette holder in synchronism with the speed of travel of the X-ray source responsive to the rotation of the rotary arm.

4 Claims, 3 Drawing Figures

FILM CASSETTE DRIVE MECHANISM IN DENTAL RADIOGRAPHIC APPARATUS FOR PHOTOGRAPHING ENTIRE JAWS

BACKGROUND OF THE INVENTION

1. Field of the Invention

This invention relates generally to a film cassette drive mechanism in a dental radiographic apparatus for photographing the entire jaws of the human body and more particularly to a type of dental radiographic apparatus in which the film cassette is of a flat form and can be moved linearly in the direction of rotation of a rotary arm.

2. Prior Art

A description will now be given, by way of example, of this type of radiographic apparatus heretofore in use and the film cassette drive mechanism used therein with reference to FIG. 1 in conjunction with the disadvantages inherent in the apparatus and mechanism.

In the figure, the numeral 1 designates a rotary arm which turns on its axis while describing a curved (for example, an elliptic) orbit approximate to the dental arch by a rotating shaft 23. The arm 1 has an X-ray source 16 and a film holder 13 immovably fixed respectively to one end thereof and to the other end thereof with the source and the holder placed in an opposed relation to each other. A platelike radiographic film cassette 14 is held in the film holder 13 and it is well known that a tomogram is made of the dental arch by the cassette 14 being moved linearly so as to be brought into synchronism with the travelling speed of the X-ray source 16 which follows the rotation on the arm 1. The drive mechanism of the cassette 14 shown in the figure includes a pulley 17 connected coaxially with the rotating shaft 23, a film holder 13 formed into a rectangular box shape having a linear distance sufficient to move the cassette 14 linearly continuously in one direction in the range of a certain speed during a period of time from beginning to start of radiographic photographing, pulleys 18 . . . for a change of direction disposed inside the holder 13, a film cassette 14 likewise disposed in the holder 13 so as to freely travel therein, and endless wires 19 wound on the pulley 17 and distributed in front and in rear in the direction of travel of the cassette by the pulleys 18 . . . for change of direction and connected to the front and rear end faces on the top of the cassette 14, and the drive mechanism functions in the manner that the cassette 14 is caused to continuously travel from one side to the other side of the film holder 13 in response to the rotation of the rotating shaft 17 and the X-ray beams is irradiated from the X-ray source 16 through a vertically long X-ray incidence slit 20 formed in the plate placed in an opposed relation to the holder 13. Incidentally, the numeral 21 designates a cover.

Referring now to the disadvantages inherent in the prior art, one of them is that the use of a pluarlity of sprockets 17, 18 . . . and wires 19 as a means for transferring the cassette 14 increases the number of parts required and makes the construction complicated in mechanism. Another of them is that since the cassette 14 is necessarily slidden into contact with the bottom plate 22 of the holder 13 while the cassette is travelling, such contact imparts a quivering movement to the film cassette, which produces adverse effects on photographing. Still another disadvantage is that, as described hereinbefore, the holder 13 must necessarily be increased in size by the fact that the holder 13 must have a linear distance necessary and sufficient to move the cassette into the holder 13 in the replacement of cassette 14.

SUMMARY OF THE INVENTION

Accordingly, it is the primary object of this invention to provide a film cassette drive mechanism in a dental radiographic apparatus for photographing the entire jaw which is free from those drawbacks mentioned above.

In keeping with the principles of this invention, the objects are accomplished by a unique structure where a variable speed motor and roller driven by the motor are used instead of the pulleys and wires and the film holder is moved by the rolling friction obtained by rolling the roller on the slide bars so that the film cassette is enabled to move together with the holder in the state of the cassette being fixed to the holder.

DETAILED DESCRIPTION OF THE INVENTION

Figure 1:
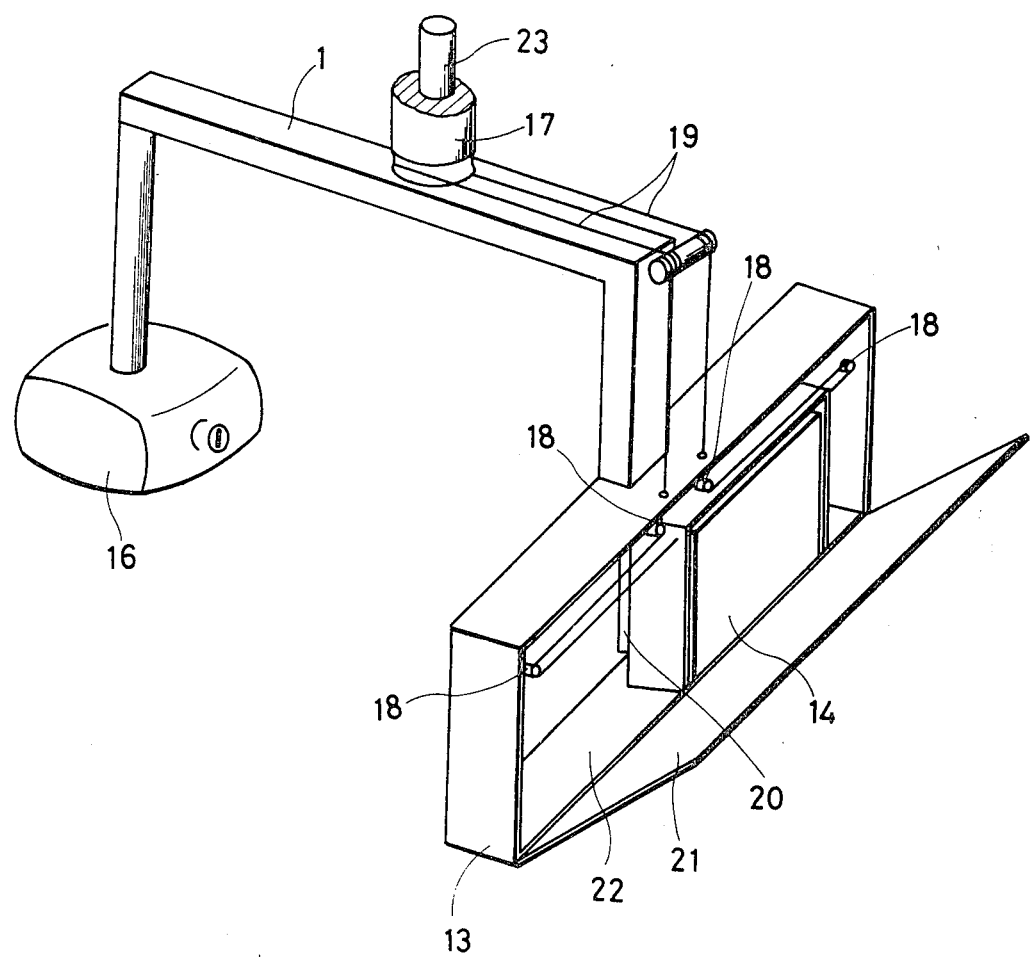
FIG. 1 is a perspective view of one example of the prior art film cassette drive mechanism.
Figure 2:
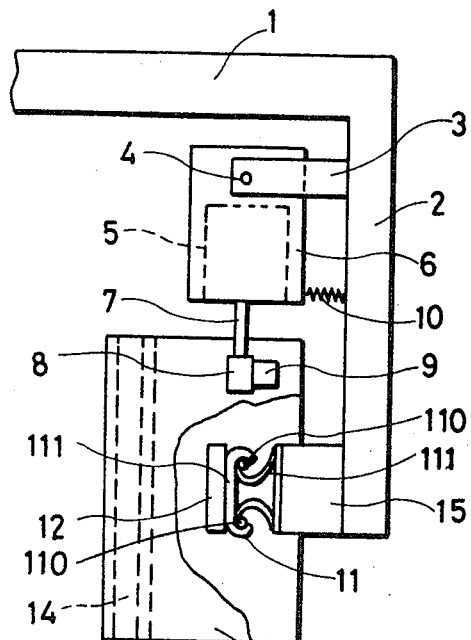
FIG. 2 is a side view, broken in part, of one embodiment of the mechanism according to the invention.
Figure 3:
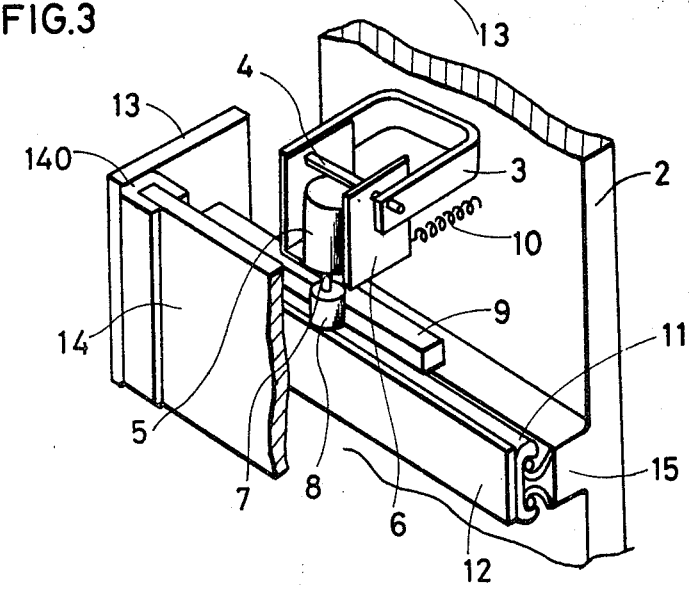
FIG. 3 is a perspective view, broken in part, of FIG. 2.

Referring in detail to the invention in a preferred form with reference to the drawings, wherein FIG. 2 is a side view, broken in part, of one embodiment of this invention, and FIG. 3 is a perspective view, broken in part, of FIG. 2.

The mechanism of this invention is a film cassette drive mechanism in a dental radiographic apparatus for photographing the entire jaws, which mechanism includes a platelike X-ray film cassette 14 fixed to a film holder 13, a slide bar 9 disposed in the direction of movement of the cassette 14, a roller 8 pressed into slidable contact with the slide bar 9, and a variable speed motor 5 driving the roller 8, wherein the film holder 13 together with the film cassette 14 is enabled by the rolling friction of the roller 8 with the slide bar 9 to move linearly in the direction of rotation of the arm 1. In the drive mechanism embodied, the slide bar 9 is mounted inside of the film holder 13, and the motor 5 is fixed inside the holder fitting portion 2 of arm by bracket 3 and fitting pin 4, and the roller is fixed coaxially to the motor shaft 7 to hold the axis of the roller 8 substantially vertically to bring the roller 8 into rolling contact with the slide bar 9 substantially in the state of the roller 8 intersecting the slide bar 9. Inside the film holder 13 is transversely disposed a protrudent bar 15, on the surface of which a linear slide bearing 11 is provided, and the slider 12 is pressed into contact with this bearing 11. The bearing 11 is conventionally known member and has balls 110 . . . interposed between longitudinal inner and outer rails 110 at longitudinal spaces thereof. Accordingly, when the slider 12 is longitudinally subjected to propulsion in the state of the slider 12 being pressed into contact with the bearing 11, the slider can linearly slide under low friction. In order to obtain rolling pressure between the roller 8 and the slide bar 9 as well as between the slider 12 and the bearing 11, a tension spring 10 is stretched between the fitting portion 2 and the motor frame 6. The film cassette 14 is fixed at both ends with respect to the film holder 13 by connecting fittings 140.

The mechanism of the invention is of the construction described above, and accordingly, when the variable speed motor 5 is driven in response to the rotation of the arm 1 so as to be brought into synchronism with the moving speed of the X-ray source 16, the roller 8 slides along the slide bar 9 in the state of the roller 8 pressing the slide bar, so that the film holder 13 together with the film cassette 14 fixed thereto continuously travels in the longitudinal direction of the bar 9. In this case, when the slider 12 fixed to the holder 13 and a linear slide bearing 11 are provided as illustrated, the travelling of the film cassette 14 is not only controlled in its guide in the direction of travelling by pressure contact of the slider 12 with the bearing 11, but also supporting of the weight of the film holder 13 can be shared also by the members 12 and 11 and hence the roller 8 and bar 9 are prevented from being given excessive weighing load. The reason for the use of a variable speed motor as the motor 5 is the need of varying an X-ray dose in accordance with the region to be examined during rotation of the arm 1. In short, the reason is that when the peripheral speed of the arm 1 is changed during the rotation of the arm 1, the travelling of the film cassette 14 must be synchronized with the changed peripheral speed. In the above, the fact that the roller 8 is pressed into slidable contact with the slider bar 9 in the state of the roller 8 substantially intersecting at right angles with the slide bar 9 brings the direction of movement of the film holder 13 into substantial agreement with the tangential direction of the roller 8 to thereby smoothen the travel of the holder 13.

As has been understood from the foregoing description, the invention can provide various advantages such as that the member necessary to move the film cassette 14 are only a variable speed motor 5, roller 8 and slide bar 9 and the number of parts used is small in comparison with the conventional mechanisms in which a plurality of pulleys, wires, etc. were used; that no adverse effect on the picture taken is produced by the fine vibration due to the slide between the roller 8 and the slide bar 9 during the movement of the cassette 14 because the cassette 14 is moved by the rolling friction between the roller 8 and the slide bar but smooth movement is made; that because both the holder 13 and the cassette 14 are moved in the state of the cassette 14 and the holder 13 being fixed to each other instead of sliding the cassette 14 inside the holder 13, there is no need of providing the holder 13 in the form of a long box which includes a space large enough to permit the movement of the cassette 14; that because the space long enough to support the cassette 14 is all that is necessary, the entire mechanism can be miniaturized; that feed of the cassette 14 can be synchronized with the speed of movement of the X-ray source 16 by the application of the variable speed motor 5; and that attachment and detachment of the cassette 14 to and from the holder 13 is facilitated. Thus, the invention is highly effective for removing the disadvantages inherent in the prior art mechanisms.

Furthermore, the embodiment illustrated in merely one example of the invention, and according to the concept of the invention, reversion of the roller 5 and slide bar 9 in their mounting positions from those shown in the drawings, substitution of projection bar 15 for the slide bar, and many other substitutions, additions, modifications may be employed.

I claim:

1. A dental radiographic apparatus for photographing the entire jaw providing an X-ray source and a film holder incorporating a platelike X-ray film cassette therein respectively at one end of a rotary arm and at the other end thereof in an opposed relation with each other and maintaining the same constantly in a mutually opposed relation by bringing the linear travelling speed of the film cassette into synchronism with the travelling speed of the X-ray source following the rotational movement of said arm so as to irradiate X-ray beams convergent from said X-ray source onto said film cassette in a state of the beams intersecting at right angles with said cassette, characterised by a film cassette drive mechanism including said platelike film cassette fixed to said film holder, a slide bar provided in the direction of travel of said cassette, a roller in rolling contact with said slide bar, and a variable motor for driving said roller, whereby said film holder together with said film cassette are enabled to move linearly along the direction of rotation of said arm through the rolling friction between said roller and said slide bar.

2. An apparatus according to claim 1, wherein said motor is mounted inside a film holder fitting portion of the arm said roller being connected coaxially to the motor shaft of said motor so as to maintain the axis of said roller substantially vertically, said slide bar being mounted inside the film holder to bring said roller into rolling contact with said slider bar in the state of the roller intersecting substantially at right angles with the bar.

3. An apparatus according to claim 1, wherein the mechanism further includes a slider substantially parallel to said slide bar and a linear slide bearing providing a travelling base of said slider.

4. An apparatus according to claim 2, wherein said slider is mounted to said film holder and said linear slide bearing is mounted to the projecting bar provided inside the holder fitting portion of said arm.

* * * * *